US010011555B2

(12) United States Patent
Lee et al.

(10) Patent No.: US 10,011,555 B2
(45) Date of Patent: *Jul. 3, 2018

(54) METHODS OF TREATING PARKINSON'S DISEASE

(71) Applicant: University of Macau, Macau (CN)

(72) Inventors: Ming Yuen Lee, Macau (CN); Zaijun Zhang, Macau (CN); Guohui Li, Macau (CN)

(73) Assignee: University of Macau, Macau (CN)

(*) Notice: Subject to any disclaimer, the term of this patent is extended or adjusted under 35 U.S.C. 154(b) by 0 days.

This patent is subject to a terminal disclaimer.

(21) Appl. No.: 15/727,638

(22) Filed: Oct. 9, 2017

(65) Prior Publication Data
US 2018/0065912 A1 Mar. 8, 2018

Related U.S. Application Data

(63) Continuation of application No. 15/260,336, filed on Sep. 9, 2016, now abandoned, which is a continuation of application No. 14/210,467, filed on Mar. 14, 2014, now Pat. No. 9,475,749.

(60) Provisional application No. 61/782,870, filed on Mar. 14, 2013.

(51) Int. Cl.
| C07C 59/52 | (2006.01) |
| A61K 31/352 | (2006.01) |
| A61K 31/192 | (2006.01) |
| C07C 51/47 | (2006.01) |
| C07C 59/90 | (2006.01) |
| C07C 59/54 | (2006.01) |
| C07C 51/347 | (2006.01) |

(52) U.S. Cl.
CPC ............ *C07C 59/52* (2013.01); *A61K 31/192* (2013.01); *A61K 31/352* (2013.01); *C07C 51/347* (2013.01); *C07C 51/47* (2013.01); *C07C 59/54* (2013.01); *C07C 59/90* (2013.01); *A61K 2300/00* (2013.01)

(58) Field of Classification Search
USPC ........................................................ 562/493
See application file for complete search history.

(56) References Cited

U.S. PATENT DOCUMENTS

| 2,720,542 | A | 10/1955 | Newhall |
| 4,022,791 | A | 5/1977 | Welch, Jr. |
| 5,434,186 | A | 7/1995 | Cohen et al. |
| 6,376,546 | B1 | 4/2002 | Shoda et al. |
| 9,475,749 | B2 * | 10/2016 | Lee ................. C07C 59/54 |
| 2009/0131384 | A1 | 5/2009 | Uysal et al. |

FOREIGN PATENT DOCUMENTS

| CN | 1071423 A | 4/1993 |
| CN | 1374965 A | 10/2002 |
| GB | 1265800 A | 3/1972 |
| JP | 03-261759 | 11/1991 |
| JP | 05-201915 | 8/1993 |
| JP | 2003509515 | 3/2003 |
| JP | 2010-505958 | 2/2010 |

OTHER PUBLICATIONS

An, L. and Guan, S., et al. (2006). "Protocatechuic acid from Alpinia oxyphylla against MPP+-induced neurotoxicity in PC12 cells." Food and chemical toxicology 44(3): 436-443.
Bitzur, S. and Kam, Z., et al. (1994). "Structure and distribution of N-cadherin in developing zebrafish embryos: morphogenetic effects of ectopic over-expression." Dev Dyn 201(2): 121-136.
Cheng, Y., G. He, et al. (2008). "Neuroprotective effect of baicalein against MPTP neurotoxicity: behavioral, biochemical and immunohistochemical profile." Neurosci Lett 441(1): 16-20.
Du, Y. and Bales, K. R., et al. (1997). "Activation of a caspase 3-related cysteine protease is required for glutamate-mediated apoptosis of cultured cerebellar granule neurons." Proceedings of the National Academy of Sciences 94(21): 11657-11662.
Graziose, R. and Lila, M. A, et al. (2010). "Merging traditional Chinese medicine with modern drug discovery technologies to find novel drugs and functional foods." Curr Drug Discov Technol 7(1): 2-12.
Im, H. I. and Joo, W.S et al. (2005). "Baicalein prevents 6-hydroxydopamine-induced dopaminergic dysfunction and lipid peroxidation in mice." J Pharmacol Sci 98(2): 185-189.
Lee, D. H and Kim, C. S., et al. (2011) Astaxanthin protects against MPTP/MPP +-induced mitochondrial dysfunction and ROS production in vivo and in vitro. Food Chem Toxicol 49(1):271-280.
Lee, H. J. and Noh, Y., et al. (2005). "Baicalein attenuates 6-hydroxydopamine-induced neurotoxicity in SH-SY5Y cells." Eur J Cell Biol 84(11): 897-905.
Levites Y. and Weinreb, O., et al. (2001) Green tea polyphenol (–)-epigallocatechin-3-gallate prevents N-methyl-4-phenyl-1,2,3,6-tetrahydropyridine-induced dopaminergic neurodegeneration. J Neurochem 78(5):1073-1082.
Li, W., Mak, et al. (2009). "Novel anti-Alzheimer's dimer Bis(7)-cognitin: cellular and molecular mechanisms of neuroprotection through multiple targets." Neurotherapeutics 6(1): 187-201.
Lin, M. T. and Beal, M.F. (2006). "Mitochondrial dysfunction and oxidative stress in neurodegenerative diseases." Nature 443(7113): 787-795.
Mandel, S. and Amit T., et al. (2007). "Iron dysregulation in Alzheimer's disease: multimodal brain permeable iron chelating drugs, possessing neuroprotective-neurorescue and amyloid precursor protein-processing regulatory activities as therapeutic agents." Prog Neurobiol 82(6): 348-360.
Mu, X. and He, G., et al. (2009). "Baicalein exerts neuroprotective effects in 6-hydroxydopamine-induced experimental parkinsonism in vivo and in vitro." Pharmacol Biochem Behav 92(4): 642-648.
Mu, X. and He, G. R., et al. (2011). "Baicalein protects the brain against neuron impairments induced by MPTP in C57BL/6 mice." Pharmacol Biochem Behav 98(2): 286-291.
Yang, M. and Sun, J., et al. (2009). "Phytochemical analysis of traditional Chinese medicine using liquid chromatography coupled with mass spectrometry." Journal of Chromatography A 1216(11): 2045-2062.
Zhang, X. and Shi, G.F., et al. (2011). "Anti-ageing effects of protocatechuic acid from Alpinia on spleen and liver antioxidative system of senescent mice." Cell Biochemistry and Function 29(4): 342-347.

(Continued)

*Primary Examiner* — Yevgeny Valenrod
(74) *Attorney, Agent, or Firm* — Eagle IP Limited; Jacqueline C. Lui

(57) ABSTRACT

This invention is directed to novel compounds isolated or derived from Alpiniae oxyphyllae fructus, chemically synthesized novel compounds, methods of preparing the novel compounds and uses thereof as neuroprotectants or drugs for treating neurodegenerative diseases such as Parkinson's disease.

9 Claims, 11 Drawing Sheets

(56) References Cited

OTHER PUBLICATIONS

Zhang, Z. J. and Cheang, L.C.V., et al. (2012). "Ethanolic Extract of Fructus Alpinia oxyphylla Protects Against 6-Hydroxydopamine-Induced Damage of PC12 Cells In Vitro and Dopaminergic Neurons in Zebrafish." Cellular and molecular neurobiology 32(1): 27-40.
Luo, J.G. et al. (2012). "Sesquiterpenoids from the fruits of Alpinia oxyphylla and inhibition of nitric oxide production in lipopolysaccaride-activated macrophases." Phytochemistry Letters 5: 134-138.
STN Columbus Registry Mar. 28, 2003.
STN Columbus Registry Feb. 23, 2014.
Ye, Q.Y. et al. (2005). "Mechanism of inflammatory factor in models of Parkinson disease due to lipopolysaccharide." Chinese Journal of Clinical Rehabilitation 9 (17): 54-56.
Newman, M. S., & Mekler, A. B. (1961). Synthesis of 7-Methyl-2, 3, 4, 5-tetrahydro-1-benzoxepin and 4-Methyl-5, 6, 7, 8-tetrahydronaphthol by Alkaline Cyclizations1. The Journal of Organic Chemistry, 26(2), 336-338.
Gutsche, C. D., & Oude-Alink, B. A. M. (1968). The photoinduced alcoholysis of 3, 4-dihydrocoumarin and related compounds. Journal of the American Chemical Society, 90(21), 5855-5861.
Inoue, S., Ikeda, H., Sato, S., et al. (1987). Improved general method of ortho alkylation of phenols using alkyl isopropyl sulfide, sulfuryl chloride, and triethylamine. An expedient synthesis of representative oxygen heterocycles and (2R, 4'R, 8'R)-.alpha.-tocopherol. The Journal of Organic Chemistry, 52(24), 5495-5497.
Kiyotsuka, Y., et al., (2009). New general method for regio- and stereoselective allylic substitution with aryl and alkenyl coppers derived from grignard reagents. J. Org. Chem. 74, 1939-1951.
Kretchmer, R., et al. (1972). The ortho alkylation of anisole. J. Org. Chem. 37 (12), 1989-1993.
Cocker, W., et al. (1960). "The elimination of non-angular alkyl groups in aromatisation reactions. Part IV." Journal of the Chemical Society: 2230.
Cocker, W., et al. (1953). "The elimination of non-angular alkyl groups in aromatisation reactions." Journal of the Chemical Society: 2355-2362.
Shimizu, T., et al. (1973). "Phenanthro[4,5-bcd]furan Derivatives. I. A Synthesis of 5-Hydroxy-1-methoxyphenanthro[4,5-bcd]furan." Bulletin of the Chemical Society of Japan 46: 1772-1776.
Ng PH B., et al. (1949). "Potential Nitrogen-Heterocycle Carcinogens. VI. Poly-Substituted 1,2-Benzocarbazoles, 1,2,5,6- and 1,2,7,8-Dibenzocarbazoles." The Journal of Organic Chemistry 15: 950-956.
Moon H., et al. (2002). "Structural requirements for the neuroprotective effects of aspirin analogues against N-methyl-D-aspartate and zinc ion neurotoxicity." Journal of Pharmacy and Pharmacology 54: 935-944.
Database Registry [online], Chemical Abstracts Service, Columbus, Ohio, US; Mar. 28, 2003, XP55289888. Retrieved from STN.

\* cited by examiner

METHODS OF TREATING PARKINSON'S DISEASE

FIELD OF INVENTION

The present invention relates to novel compounds for treatment of neurodegenerative diseases. In particular, the present invention relates to isolated and synthesized compounds, methods of isolating or preparing the compounds, use of the compounds for treating neurodegenerative diseases.

BACKGROUND OF INVENTION

Neurodegenerative disease is directed to a range of conditions which primarily affect the neurons in the human brain. Parkinson's disease (PD) is the second most common neurodegenerative disease with physiological manifestations including tremors, bradykinesia, abnormal postural reflexes, rigidity and akinesia. It results primarily from the death of dopaminergic (DA) neurons in the substantia nigra. Current therapies for PD mainly provide symptomatic improvement by replacing neurotransmitters or controlling their metabolism to restore their imbalance. Since these therapies are not altering the underlying disease process, they usually have little or no impact on disease progression.

SUMMARY OF INVENTION

It is therefore an object of the present invention to provide novel compounds for the treatment of neurodegenerative diseases, methods of preparing the compounds, their compositions and uses thereof.

Accordingly, the present invention, in one aspect, provides a compound with Formula I:

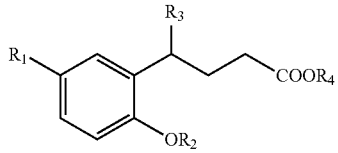

Formula I wherein $R_1$ and $R_3$ are independently selected from the group consisting of H, unsubstituted or substituted alkyl, cycloalkyl, alkenly, alkynyl, aryl, heteroaryl, carboxy, alkyloxy, hydroxyl, amino, nitro, alkylthio, acyl, cyano, acylamino, halo and ester; and $R_2$ and $R_4$ are independently selected from the group consisting of H, unsubstituted or substituted alkyl, cycloalkyl, aryl, heteroaryl, alkyoxy, acyl, acylamino and halo.

In an exemplary embodiment, for the compound with Formula I, $R_1$ and $R_3$ are independently unsubstituted or substituted (C1-C3) alkyl; and $R_2$ and $R_4$ are H.

In another exemplary embodiment, the compound with Formula I is an isolated and purified ((R)-4-(2-hydroxy-5-methylphenyl)-5-methylhexanoic acid). The compound ((R)-4-(2-hydroxy-5-methylphenyl)-5-methylhexanoic acid) is represented as the following formula (compound 1).

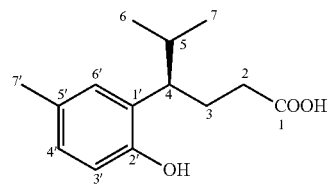

Compound 1

In a further exemplary embodiment, the compound with Formula I is ((S)-4-(2-hydroxy-5-methylphenyl)-5-methylhexanoic acid) or (4-(2-hydroxy-5-methylphenyl)-5-methylhexanoic acid). The compounds ((S)-4-(2-hydroxy-5-methylphenyl)-5-methylhexanoic acid) (compound 4) and (4-(2-hydroxy-5-methylphenyl)-5-methylhexanoic acid) (compound 5) are represented as the below formulae, respectively.

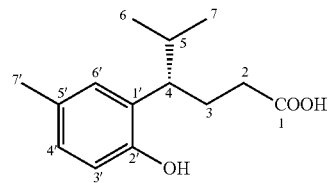

Compound 4

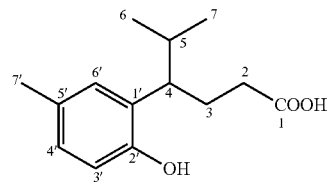

Compound 5

In yet another aspect, the present invention provides a composition comprising the compound with Formula I and a pharmaceutically acceptable salt or carrier.

Another aspect of the present invention provides use of the compound with Formula I for protection against neural damage.

Another aspect of the present invention provides use of the compound with Formula I for treatment of neurodegenerative disease.

In an exemplary embodiment, the neurodegenerative disease is Parkinson's disease.

Another aspect of the present invention provides a method of treating Parkinson's disease, or protecting against neural damage or neural cells loss, comprising the step of administering the compound with Formula I to a subject in need.

Another aspect of the present invention provides a method of treating neurodegenerative disease in a human patient comprising administrating to the patient a therapeutically effective amount of the compound with Formula I and chrysin, wherein the compound exhibits a synergistic effect with chrysin for neuroprotective effect.

Another aspect of the present invention provides a compound with Formula II:

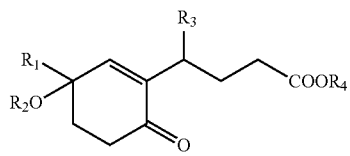

Formula II wherein $R_1$ and $R_3$ are independently selected from the group consisting of H, unsubstituted or substituted alkyl, cycloalkyl, alkenly, alkynyl, aryl, heteroaryl, carboxy, alkyloxy, hydroxyl, amino, nitro, alkylthio, acyl, cyano, acylamino, halo and ester; and $R_2$ and $R_4$ are independently selected from the group consisting of H, unsubstituted or substituted alkyl, cycloalkyl, aryl, heteroaryl, alkyoxy, acyl, acylamino and halo.

In an exemplary embodiment, for the compound with Formula II, $R_1$ and $R_3$ are independently unsubstituted or substituted (C1-C3) alkyl; and $R_2$ and $R_4$ are H.

In a further exemplary embodiment, the compound with Formula II is an isolated and purified ((4S)-4-(3-hydroxy-3-methyl-6-oxocyclohex-1-enyl)-5-methylhexanoic acid) or ((4R)-4-(3-hydroxy-3-methyl-6-oxocyclohex-1-enyl)-5-methylhexanoic acid). The compounds ((4S)-4-(3-hydroxy-3-methyl-6-oxocyclohex-1-enyl)-5-methylhexanoic acid) (compound 2) and ((4R)-4-(3-hydroxy-3-methyl-6-oxocyclohex-1-enyl)-5-methylhexanoic acid) (compound 3) are represented as the following formulae, respectively.

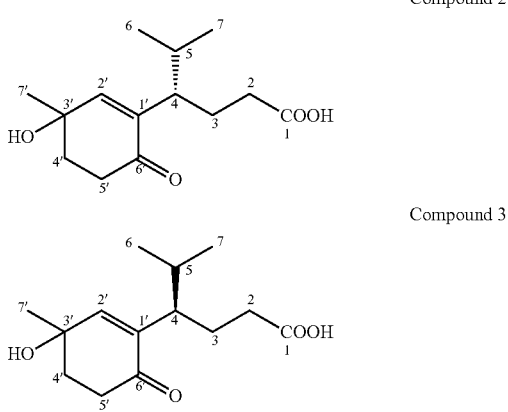

Compound 2

Compound 3

Another aspect of the present invention provides a composition comprising the compound with Formula II and a pharmaceutically acceptable salt or carrier.

Another aspect of the present invention provides use of the compound with Formula II for protection against neural damage.

Another aspect of the present invention provides use of the compound with Formula II for treatment of neurodegenerative disease.

In an exemplary embodiment, the neurodegenerative disease is Parkinson's disease.

Another aspect of the present invention provides a method of treating Parkinson's disease, or protecting against neural damage or neural cells loss, comprising the step of administering the compound with Formula II to a subject in need.

Another aspect of the present invention provides a method for preparing an isolated and purified compound from A. oxyphyllae fructus, comprising the steps of:

a) extracting samples of A. oxyphyllae fructus with aqueous alcohol solution under low pressure hot reflux and removing the solvent to obtain a crude extract;

b) reconstituting the crude extract in step (a) with ethanol to obtain ethanol extract solution;

c) absorbing the ethanol extract solution into silica gel and removing ethanol to obtain silica gel extract;

d) extracting the silica gel extract with organic solvents successively under normal pressure hot reflux to obtain bioactive parts;

e) fractionating the bioactive parts and eluting with solvent mixture with increasing polarity to obtain a first bioactive fraction f) purifying the first bioactive fraction of step (e) to obtain the compound;

wherein the compound is selected from the group consisting of ((R)-4-(2-hydroxy-5-methylphenyl)-5-methylhexanoic acid), ((4S)-4-(3-hydroxy-3-methyl-6-oxocyclohex-1-enyl)-5-methylhexanoic acid) and ((4R)-4-(3-hydroxy-3-methyl-6-oxocyclohex-1-enyl)-5-methylhexanoic acid).

In an exemplary embodiment, the step (f) further comprises g) fractioning the first bioactive fraction of step (e) and eluting with solvent mixture with increasing polarity to obtain a second bioactive portion h) purifying the second bioactive portion with isocratic elution to obtain the compound ((R)-4-(2-hydroxy-5-methylphenyl)-5-methylhexanoic acid).

In an exemplary embodiment, the step (f) further comprises purifying the first bioactive fraction of step (e) by preparative high performance liquid chromatography with isocratic elution to obtain the compound ((4S)-4-(3-hydroxy-3-methyl-6-oxocyclohex-1-enyl)-5-methylhexanoic acid) and the compound ((4R)-4-(3-hydroxy-3-methyl-6-oxocyclohex-1-enyl)-5-methylhexanoic acid).

DETAILED DESCRIPTION OF THE PREFERRED EMBODIMENTS

Figure 1:
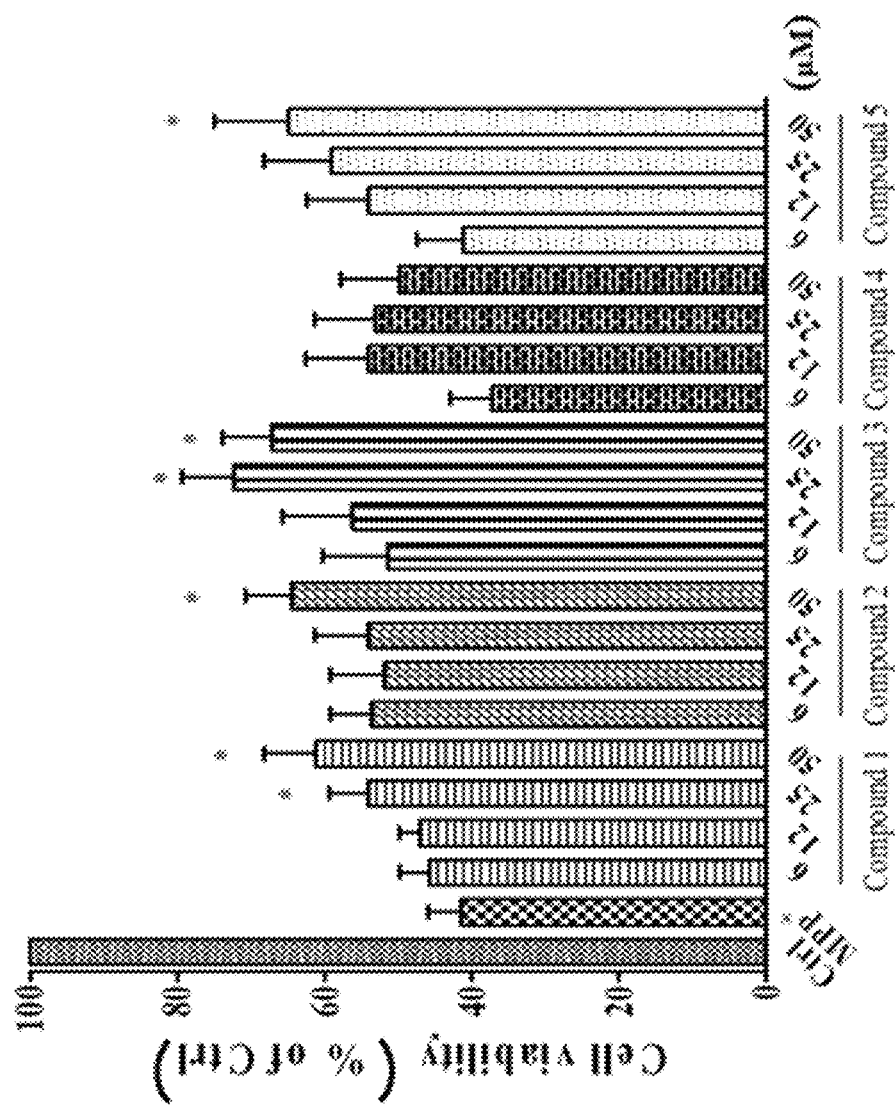
FIG. 1 shows the neuroprotective effects of compounds 1-5 on $MPP^+$-induced primary CGNs damage. $*p<0.05$ compared with $MPP^+$ treatment alone group.

As used herein and in the claims, "comprising" means including the following elements but not excluding others.

The following examples are given by way of illustration of the present invention but should not be considered to limit the scope of the invention. Reasonable variations, such as those understood by reasonable artisans, can be made without departing from the scope of the present invention.

EXAMPLE 1 Physical-Chemical Properties of Compounds 1-5

1. Physical-Chemical Properties of Compound 1

((R)-4-(2-hydroxy-5-methylphenyl)-5-methylhexanoic acid)

Formula:

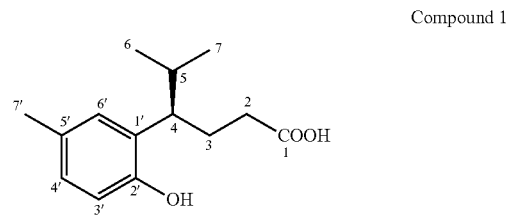 [SMILES: Cc1ccc(O)c([C@H](CCC(=O)O)C(C)C)c1]

Compound 1

Physical description: White powder
Specific rotation: $[\alpha]_D^{26.2}=-11.3$ (c 3.0, MeOH), $[\alpha]_D^{25.0}=-19.4$ (c 0.72, $CH_2Cl_2$).
UV (methanol) λ max: 222 nm, 282 nm
$^1$H NMR spectrum (600 MHz, $CDCl_3$, $\delta_{TMS}$=0.00 ppm):
δ (ppm) 2.18, 2.11 (2H, m, H-2α, 2β), 1.80, 2.17 (2H, m, H-3α, 3β), 2.67 (1H, m, H-4), 1.85 (1H, m, H-5), 1.01 (3H, d, J=6.58 Hz, H-6), 0.74 (3H, d, J=6.65 Hz, H-7), 6.66 (1H, d, J=8.52 Hz, H-3'), 6.85 (1H, d, J=8.52 Hz, H-4'), 6.85 (1H, s, H-6'), 2.27 (3H, s, H-7')
$^{13}$C NMR spectrum (125 MHz, $CDCl_3$, $\delta_{TMS}$=0.00 ppm):
δ (ppm) 178.2 (C-1), 31.7 (C-2), 27.6 (C-3), 44.1 (C-4), 32.7 (C-5), 20.8 (C-6), 21.1 (C-7), 130.1 (C-1'), 151.9 (C-2'), 115.4 (C-3'), 127.4 (C-4'), 129.5 (C-5'), 128.2 (C-6'), 20.6 (C-7')
Mass spectrum (HR-ESI-MS): m/z 235.1369 [M−H]$^-$ (calcd for $C_{14}H_{19}O_3$, 235.1339)

2. Physical-Chemical Properties of Compound 2

(4S)-4-(3-hydroxy-3-methyl-6-oxocyclohex-1-enyl)-5-methylhexanoic acid

Formula:

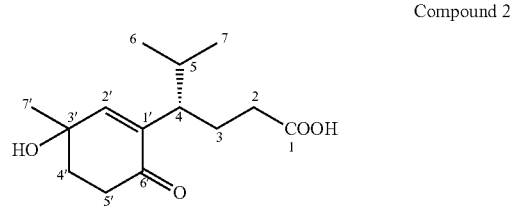 [SMILES: CC(C)[C@H](CCC(=O)O)C1=CC(C)(O)CCC1=O]

Compound 2

Physical description: yellow oil
Specific rotation: $[\alpha]_D^{26.2}=-22.5$ (c 3.0, MeOH)
UV (methanol) λ max: 238 nm
$^1$H NMR spectrum (600 MHz, $CDCl_3$, $\delta_{TMS}$=0.00 ppm):
δ (ppm) 2.18, 2.16 (2H, m, H-2), 1.97, 1.74 (2H, m, H-3α, 3β), 2.25 (1H, m, H-4), 1.79 (1H, m, H-5), 0.76 (3H, d, J=6.68 Hz, H-6), 0.89 (3H, d, J=6.65 Hz, H-7), 6.40 (1H, s, H-2'), 2.65, 2.64 (2H, m, H-4'α, 4β), 2.09 (2H, m, H-5'), 1.45 (3H, s, H-7')
$^{13}$C NMR spectrum (125 MHz, $CDCl_3$, $\delta_{TMS}$=0.00 ppm):
δ (ppm) 178.3 (C-1), 45.5 (C-2), 25.6 (C-3), 45.3 (C-4), 31.2

(C-5), 20.4 (C-6), 21.0 (C-7), 139.0 (C-1'), 150.6 (C-2'), 69.0 (C-3'), 35.4 (C-4'), 37.1 (C-5'), 198.6 (C-6'), 27.6 (C-7')

Mass spectrum (HR-ESI-MS): m/z 253.1468 [M−H]⁻ (calcd for $C_{14}H_{21}O_4$, 253.1445)

3. Physical-Chemical Properties of Compound 3

((4R)-4-(3-hydroxy-3-methyl-6-oxocyclohex-1-enyl)-5-methylhexanoic acid)

Formula:

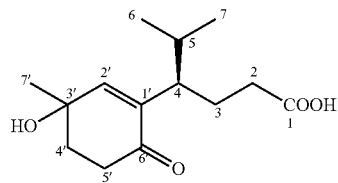

Compound 3

Physical description: yellow oil
Specific rotation: $[\alpha]_D^{26.2}=-31.5$ (c 3.0, MeOH)
UV (methanol) λ max: 238 nm
¹H NMR spectrum (600 MHz, CDCl₃, $\delta_{TMS}=0.00$ ppm):
δ (ppm) 2.16 (2H, m, H-2), 1.95, 1.65 (2H, m, H-3α, 3β), 2.53 (1H, m, H-4), 1.79 (1H, m, H-5), 0.77 (3H, d, J=6.68 Hz, H-6), 0.86 (3H, d, J=6.65 Hz, H-7), 6.44 (1H, s, H-2'), 2.66, 2.44 (2H, m, H-4'α, 4'β), 2.10 (2H, m, H-5'), 1.46 (3H, s, H-7')
¹³C NMR spectrum (125 MHz, CDCl₃, $\delta_{TMS}=0.00$ ppm):
δ (ppm) 178.2 (C-1), 32.1 (C-2), 25.7 (C-3), 42.1 (C-4), 31.9 (C-5), 20.4 (C-6), 20.4 (C-7), 139.1 (C-1'), 149.6 (C-2'), 69.1 (C-3'), 37.0 (C-4'), 35.2 (C-5'), 198.7 (C-6'), 27.5 (C-7')

Mass spectrum (HR-ESI-MS): m/z 253.1480 [M−H]⁻ (calcd for $C_{14}H_{21}O_4$, 253.1445)

4. Physical-Chemical Properties of Compound 4

(S)-4-(2-hydroxy-5-methylphenyl)-5-methylhexanoic acid

Formula:

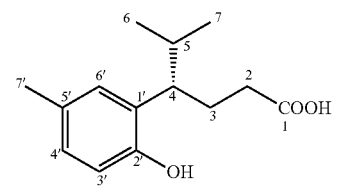

Compound 4

Physical description: White powder
Specific rotation: $[\alpha]_D^{25.0}=+20.0$ (c, 0.72, CH₂Cl₂)
¹H NMR spectrum (600 MHz, CDCl₃, $\delta_{TMS}=0.00$ ppm):
δ (ppm) 2.20, 2.13 (2H, m, H-2α, 2β), 1.81, 2.18 (2H, m, H-3α, 3β), 2.67 (1H, m, H-4), 1.86 (1H, m, H-5), 1.02 (3H, d, J=6.5 Hz, H-6), 0.74 (3H, d, J=6.5 Hz, H-7), 6.65 (1H, d, J=8.5 Hz, H-3'), 6.84 (2H, d, J=8.5 Hz, H-4'), 6.84 (1H, s, H-6'), 2.24 (3H, s, H-7')
¹³C NMR spectrum (125 MHz, CDCl₃, $\delta_{TMS}=0.00$ ppm):
δ (ppm) 180.2 (C-1), 32.2 (C-2), 27.6 (C-3), 44.3 (C-4), 32.9 (C-5), 20.9 (C-6), 21.3 (C-7), 130.1 (C-1'), 151.8 (C-2'), 115.6 (C-3'), 127.4 (C-4'), 129.4 (C-5'), 128.6 (C-6'), 20.8 (C-7')

Mass spectrum (HR-ESI-MS): m/z 235.1358 [M−H]⁻ (calcd for $C_{14}H_{19}O_3$, 235.1339)

5. Physical-Chemical Properties of Compound 5

(4-(2-hydroxy-5-methylphenyl)-5-methylhexanoic acid)

Formula:

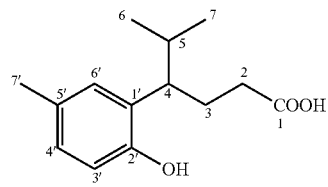

Compound 5

Physical description: White powder
¹H NMR spectrum (600 MHz, CDCl₃, $\delta_{TMS}=0.00$ ppm):
δ (ppm) 2.20, 2.13 (2H, m, H-2α, 2β), 1.82, 2.18 (2H, m, H-3α, 3β), 2.66 (1H, m, H-4), 1.87 (1H, m, H-5), 1.02 (3H, d, J=6.5 Hz, H-6), 0.74 (3H, d, J=6.5 Hz, H-7), 6.65 (1H, d, J=8.5 Hz, H-3'), 6.85 (1H, d, J=8.5 Hz, H-4'), 6.85 (1H, s, H-6'), 2.24 (3H, s, H-7')
¹³C NMR spectrum (125 MHz, CDCl₃, $\delta_{TMS}=0.00$ ppm):
δ (ppm) 180.2 (C-1), 32.2 (C-2), 27.6 (C-3), 44.3 (C-4), 32.9 (C-5), 20.7 (C-6), 21.3 (C-7), 130.1 (C-1'), 151.8 (C-2'), 115.6 (C-3'), 127.4 (C-4'), 129.4 (C-5'), 128.6 (C-6'), 20.9 (C-7')

EXAMPLE 2 Method of Isolating Compound 1 from *A. oxyphyllae* Fructus

After coarsely pulverized, air-dried fruits of *A. oxyphyllae* fructus were extracted with 95% aqueous alcohol solution under reflux for three times, the extract solution was dried by rotary evaporator in a water bath. The dried crude extracts of *A. oxyphyllae* fructus were then suspended in ethanol and absorbed into the silica gel. After removal of ethanol, the dried silica gel was successively extracted with petroleum ether, ethyl acetate and ethanol to yield petroleum ether part, ethyl acetate part and ethanol part respectively. Bioassay showed that the ethyl acetate part is the most bioactive and thus selected for further analysis. The ethyl acetate part was subjected for further separation by normal-phase silica gel column chromatography with chloroform mixed with increasing amount of methanol from 0% to 20% to yield 13 fractions (Fractions A-M). Bioassay showed that fraction G is the most bioactive. Fraction G was fractionated by silica gel column chromatography eluting chloroform mixed with increasing amount of methanol from 0% to 2% to yield five major sub-fractions GS1, GS2, GS3, GS4 and GS5. Sub-fraction GS2 was further fractionated by sephadex LH-20 and compound 1 was obtained from an elution using 100% methanol. The purity of compound 1 was monitored by thin layer chromatography with iodine as indicator.

EXAMPLE 3 Method of Isolating Compounds 2 and 3 from *A. oxyphyllae* Fructus

As presented in example 2, the most active fraction G was fractionated by preparative high performance liquid chromatography and compounds 2 and 3 were obtained by an elution with 25% acetonitrile. The purity of compounds 2 and 3 was monitored by UV at 254 nm.

The present invention provides evidences to support the use of compounds 1, 2 and 3 as reference chemical markers for controlling the quality of *A. oxyphyllae* fructus.

EXAMPLE 4 Method of Synthesizing Compounds 1, 4 and 5

Compound 1 together with its chiral isomer compound 4 and racemic compound 5 were synthesized as scheme (I) shows:

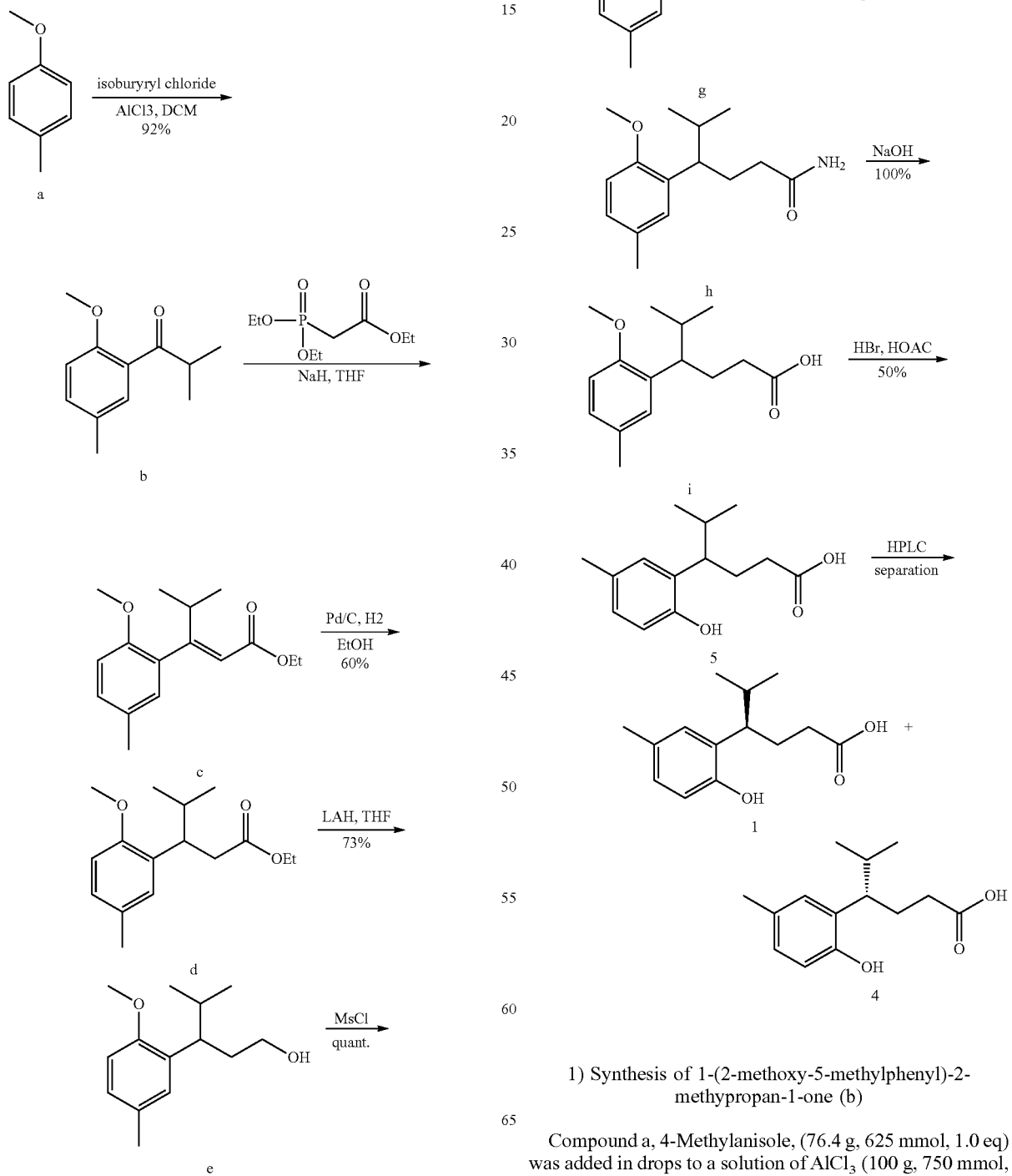

1) Synthesis of 1-(2-methoxy-5-methylphenyl)-2-methypropan-1-one (b)

Compound a, 4-Methylanisole, (76.4 g, 625 mmol, 1.0 eq) was added in drops to a solution of $AlCl_3$ (100 g, 750 mmol, 1.2 eq) in DCM (1000 mL) at 0° C., then isoburyryl chloride (80.0 g, 750 mmol, 1.2 eq) was added dropwise to the solution while keeping temperature below 5° C. The mixture was stirred at room temperature for overnight. The mixture was then poured into crush ice (2.0 kg); the organic layer was washed by with $H_2O$ and saturated aqueous NaCl, dried over $Na_2SO_4$, filtered, and finally dried to give compound b (110 g, 92%) as brown oil.

$^1$H NMR (400 MHz, CDCl$_3$): δ 1.14 (d, J=6.8 Hz, 6H), 2.05 (s, 3H), 3.44-3.51 (m, 1H), 3.85 (s, 3H), 6.85 (d, J=8.4 Hz, 1H), 7.22 (d, J=8.4 Hz, 1H), 7.31 (s, 1H).

2) Synthesis of ethyl-(2E)-3-(2-methyloxy-5-methylphenyl)-4-methypent-2-enoate (c)

To a suspension of NaH (34.3 g, 858 mmol, 1.5 eq, 60% in mineral oil) in THF (1000 mL) triethyl phosphonoacetate (192 g, 858 mmol, 1.5 eq) was added dropwise while keeping temperature below 10° C. for 40 mins, the solution was then stirred at 0° C. for 30 mins. Compound b (110 g, 572 mmol, 1.0 eq) was added drop by drop while keeping temperature below 10° C. for 20 mins. The mixture was refluxed overnight. The reaction was quenched by aqueous $NH_4Cl$, the organic layer obtained was washed by with $H_2O$ and saturated aqueous NaCl; dried over $Na_2SO_4$, filtered, and evaporated, the residue was purified by column chromatography on silica gel (PE/EtOAc=100/1~30/1) to give crude compound c (150 g) as a colorless oil, which contained compound b and compound c.

$^1$H NMR (400 MHz, CDCl$_3$): δ 0.81-1.18 (m, 9H), 2.20 (s, 3H), 2.53-2.59 (m, 1H), 3.67 (s, 3H), 3.89 (q, J=7.2 Hz, 2H), 5.83 (s, 1H), 6.67 (s, 1H), 6.71 (d, J=8.4 Hz, 1H), 6.98 (d, J=8.4 Hz, 1H).

3) Synthesis of ethyl 3-(2-methyloxy-5-methylphenyl)-4-methypentanoate (d)

A mixture of compound c (150 g, crude) and Pd/C (15 g, 10%) in EtOH (500 mL) was stirred overnight at room temperature under $H_2$ atmosphere and then filtered. The filtrate was evaporated to give crude compound d (110 g, 61% yield for 2 steps) as a colorless oil, which contained compound d (84%, w/w) and compound b (16%, w/w).

$^1$H NMR (400 MHz, CDCl$_3$): δ 0.76 (d, J=6.8 Hz, 3H), 0.79 (d, J=6.8 Hz, 3H), 1.06 (t, J=7.2 Hz, 3H), 1.92-1.97 (m, 1H), 2.25 (s, 3H), 2.61-2.75 (m, 2H), 3.22-3.28 (m, 1H), 3.77 (s, 3H), 3.95 (q, J=7.2 Hz, 2H), 6.72 (d, J=8.4 Hz, 1H), 6.88 (s, 1H), 6.94 (d, J=8.4 Hz, 1H).

4) Synthesis of 3-(2-methyloxy-5-methylphenyl)-4-methypentanl-1-ol (e)

Compound d (80.0 g, 255 mmol, 1.0 eq, 84% w/w) was added dropwise to a suspension of LAH (13.8 g, 363 mmol, 1.43 eq) in THF (500 mL) at 0° C. over 30 mins and then stirred at room temperature for 1.5 hrs. The reaction was successively quenched by $H_2O$ (13.8 g), aqueous NaOH (13.8 mL, 15%) and $H_2O$ (41.4 g), then filtered via celite and concentrated. The residue was purified by column chromatography on silica gel (PE/EtOAc=50/1~20/1) to give compound e (41.4 g, 73%) as a colorless oil.

$^1$H NMR (300 MHz, CDCl$_3$): δ 0.73 (d, J=6.6 Hz, 3H), 1.03 (d, J=6.6 Hz, 3H), 1.27-1.65 (m, 1H), 1.87-1.94 (m, 2H), 2.10-2.17 (m, 1H), 2.29 (s, 3H), 2.86-2.93 (m, 1H), 3.21-3.24 (m, 1H), 3.26-3.50 (m, 1H), 3.80 (s, 3H), 6.78 (d, J=8.1 Hz, 1H), 6.93 (s, 1H), 6.97 (d, J=8.1 Hz, 1H).

5) Synthesis of 3-(2-methyloxy-5-methylphenyl)-4-methypentyl methylsulfonate (f)

MsCl (42.6 g, 558 mmol, 2.0 eq) was added in drops to a solution of compound e (41.4 g, 186 mmol, 1.0 eq) and TEA (56.5 g, 558 mmol, 3.0 eq) in DCM (750 mL) at 0° C. and the solution was stirred for 2 hrs at room temperature. After 2 hrs, the mixture was washed with $H_2O$ and then aqueous NaCl, dried over $Na_2SO_4$, filtered, and evaporated to give compound f (55.8 g, 100%) as a brown oil.

$^1$H NMR (400 MHz, CDCl$_3$): δ 0.72 (d, J=6.4 Hz, 3H), 0.97 (d, J=6.4 Hz, 3H), 1.84-1.91 (m, 1H), 1.97-2.06 (m, 1H), 2.18-2.26 (m, 4H), 2.83-3.14 (m, 4H), 3.75 (s, 3H), 3.88-3.94 (m, 1H), 4.00-4.05 (m, 1H), 6.74 (d, J=8.4 Hz, 1H), 6.86 (s, 1H), 6.96 (d, J=8.4 Hz, 1H).

6) Synthesis of 4-(2-methyloxy-5-methylphenyl)-5-methylhexanenitrile (g)

A mixture of compound f (55.8 g, 186 mmol, 1.0 eq) and NaCN (18.2 g, 372 mmol, 2.0 eq) in DMF (300 mL) was stirred at 75° C. overnight and distributed into EtOAc and $H_2O$. The organic layer was washed with $H_2O$ and saturated aqueous NaCl, dried over $Na_2SO_4$, filtered, and evaporated to give compound g (38.5 g, 90%) as a colorless oil.

$^1$H NMR (400 MHz, CDCl$_3$): δ 0.71 (d, J=6.8 Hz, 3H), 0.99 (d, J=6.8 Hz, 3H), 1.85-2.17 (m, 5H), 2.28 (s, 3H), 2.75-2.81 (m, 1H), 3.76 (s, 3H), 6.75 (d, J=8.4 Hz, 1H), 6.84 (s, 1H), 6.98 (d, J=8.4 Hz, 1H).

7) Synthesis of 4-(2-methyloxy-5-methylphenyl)-5-methylhexanamide (h)

$H_2O_2$ (32.0 g, 282 mmol, 1.5 eq, 30% in $H_2O$) was added dropwise to a suspension of compound g (43.5 g, 188 mmol, 1.0 eq) and $K_2CO_3$ (10.4 g, 75.2 mmol, 0.4 eq) in DMSO (220 mL) at room temperature, the solution was then stirred at room temperature for 3 hrs. Additional $H_2O_2$ (32.0 g, 282 mmol, 1.5 eq, 30% in $H_2O$) was added dropwise at room temperature for 1 hr. The mixture was separated between EtOAc and $H_2O$, the organic layer was washed with $H_2O$ and then saturated aqueous NaCl, dried over $Na_2SO_4$, filtered, and evaporated to give compound h (46.9 g, 100%) as a white solid.

$^1$H NMR (300 MHz, CDCl$_3$): δ 0.72 (d, J=6.6 Hz, 3H), 1.00 (d, J=6.6 Hz, 3H), 1.73-2.21 (m, 5H), 2.28 (s, 3H), 2.79-2.84 (m, 1H), 3.79 (s, 3H), 5.38 (brs, 2H), 6.76 (d, J=8.4 Hz, 1H), 6.85 (s, 1H), 6.97 (d, J=8.4 Hz, 1H).

8) Synthesis of 4-(2-methyloxy-5-methylphenyl)-5-methylhexanoic acid (i)

A mixture of compound h (46.9 g, 188 mmol, 1.0 eq), NaOH (30.1 g, 752 mmol, 4.0 eq) and $H_2O$ (100 mL) in EtOH (400 mL) was refluxed overnight and concentrated. pH of the residue was adjusted with 1N HCl to 2, the residue was then extracted with EtOAc. The organic layer was washed with aqueous NaCl, dried over $Na_2SO_4$, filtered, and evaporated to give compound i (47.1 g, 100%) as a brown oil.

$^1$H NMR (300 MHz, CDCl$_3$): δ 0.74 (d, J=6.6 Hz, 3H), 1.01 (d, J=6.6 Hz, 3H), 1.78-1.94 (m, 2H), 2.04-2.20 (m, 3H), 2.28 (s, 3H), 2.76-2.82 (m, 1H), 3.76 (s, 3H), 6.76 (d, J=8.4 Hz, 1H), 6.89 (s, 1H), 6.97 (d, J=8.4 Hz, 1H).

9) Synthesis of (R)-4-(2-hydroxy-5-methylphenyl)-5-methylhexanoic acid (1) and (S)-4-(2-hydroxy-5-methylphenyl)-5-methylhexanoic acid (4)

HBr (235 mL, 33% in AcOH) solution was added to a solution of compound i (47.1 g, 188 mmol) in AcOH (235 mL) dropwise at room temperature, then refluxed overnight. The mixture was diluted with EtOAc and $H_2O$. The organic layer was washed with $H_2O$ and saturated aqueous NaCl, and subsequently concentrated. The residue was diluted with EtOH (400 ml) and $H_2O$ (40 mL) with $LiOH.H_2O$ (31.6 g, 752 mmol) added; the mixture was stirred for 1.5 hours at room temperature and then concentrated. The residue was diluted, and acidified with 1N HCl to pH 2-3. The organic layer was washed by $H_2O$, and then aqueous NaCl, dried over $Na_2SO_4$, filtered, and evaporated. The residue was purified by column chromatography on silica gel (PE/EtOAc=100/1 to 10/1) to give compound 5 (22.2 g, 50%) as a white solid. 11.0 g of 5 was separated by Chiral Prep-HPLC to give 4.5 g of compound 1 and 3.8 g of compound 4.

Compound 1: $^1H$ NMR (400 MHz, DMSO-d6): δ 0.68 (d, J=6.4 Hz, 3H), 0.92 (d, J=6.4 Hz, 3H), 1.68-1.97 (m, 5H), 2.17 (s, 3H), 2.65-2.68 (m, 1H), 6.66 (d, J=7.6 Hz, 1H), 6.76-6.79 (m, 2H), 8.83 (s, 1H), 11.84 (s, 1H); $^1H$ NMR (600 MHz, $CDCl_3$, $δ_{TMS}$=0.00 ppm): δ 6.66 (d, J=8.52 Hz, 2H), 6.85 (d, J=8.52 Hz, 2H), 6.85 (s, 1H), 2.67 (m, 1H), 1.80, 2.17 (m, 2H), 2.18, 2.11 (m, 2H), 1.85 (m, 1H), 1.01 (d, J=6.58 Hz, 3H), 0.74 (d, J=6.65 Hz, 3H), 2.27 (s, 3H); LCMS [mobile phase: from 95% water (0.01% $NH_4Ac$) and 5% $CH_3CN$ to 5% water (0.01% $NH_4Ac$) and 95% $CH_3CN$ in 6 min, finally under these conditions for 0.5 min.] purity is >95%, Rt=3.847 min; MS Calcd.: 236; MS Found: 237 ([M+H]$^+$); Chiral HPLC (Chiralcel OJ-H column): Rt=7.16 min (Hex/t-ButOH/TFA=95:5:0.3), ee=100%; $[α]_D^{25}$=−19.4 (c 0.72, $CH_2Cl_2$).

Compound 4: $^1H$ NMR (400 MHz, DMSO-$d_6$): δ 0.68 (d, J=6.4 Hz, 3H), 0.92 (d, J=6.4 Hz, 3H), 1.66-2.01 (m, 5H), 2.17 (s, 3H), 2.65-2.67 (m, 1H), 6.66 (d, J=8.4 Hz, 1H), 6.76-6.79 (m, 2H), 8.79-8.84 (brs, 1H), 11.79-11.86 (brs, 1H); $^1H$ NMR (600 MHz, $CDCl_3$, $δ_{TMS}$=0.00 ppm): δ 6.65 (d, J=8.5 Hz, 2H), 6.84 (d, J=8.5 Hz, 2H), 6.84 (1H, s, H-5), 2.67 (m, 1H), 1.81, 2.18 (m, 2H), 2.20, 2.13 (m, 2H), 1.86 (m, 1H), 1.02 (d, J=6.5 Hz, 3H), 0.74 (d, J=6.5 Hz, 3H), 2.24 (s, 3H); LCMS [mobile phase: from 95% water (0.01% $NH_4Ac$) and 5% $CH_3CN$ to 5% water (0.01% $NH_4Ac$) and 95% $CH_3CN$ in 6 min, finally under these conditions for 0.5 min.] purity is >95%, Rt=3.849 min; MS Calcd.: 236; MS Found: 237 ([M+H]$^+$); Chiral HPLC (Chiralcel OJ-H column): rt=10.24 min (Hex/t-ButOH/TFA=95:5:0.3; enantiomer: Rt=7.31 min), ee=98%; $[α]_D^{25}$=+20.0 (c 0.72, $CH_2Cl_2$)

Compound 5: $^1H$ NMR spectrum (600 MHz, $CDCl_3$, $δ_{TMS}$=0.00 ppm): δ 6.65 (d, J=8.5 Hz, 2H), 6.85 (d, J=8.5 Hz, 2H), 6.85 (s, 1H), 2.66 (m, 1H), 1.82, 2.18 (m, 2H), 2.20, 2.13 (m, 2H), 1.87 (m, 1H), 1.02 (d, J=6.5 Hz, 3H), 0.74 (d, J=6.5 Hz, 3H), 2.24 (s, 3H)

EXAMPLE 5 Study on the Effects in Protection Against MPP$^+$ Induced CGNs Damage N-methyl-4-phenyl-1,2,3,6-tetrahydropyridine (MPTP) is the precursor of 1-methyl-4-phenylpyridinium (MPP$^+$), a mitochondrial electron-transport chain (ETC) complex I inhibitor generated from MPTP by the dopaminergic catabolic enzyme monoamine oxidase B. Accumulation of MPP$^+$ in dopaminergic neurons results in ATP deficiency, collapse of the mitochondrial membrane potential, opening of the mitochondrial permeability transition pore (mPTP), and production of ROS, leading to apoptosis. MPTP/MPP$^+$ has been widely used in in vitro and in vivo neuronal damage to model dopaminergic neurodegeneration characteristic of Parkinson's disease.

Primary cerebellar granule neurons (CGNs) were prepared from 8 days old Sprague-Dawley rats, as described in a previous publication (Du, Bales et al. 1997). CGNs cultured in vitro for 7 days were pre-treated with serial concentrations of compounds 1-5 from 6 μM to 50 μM respectively for 2 hours, vehicle group was incubated with 0.1% DMSO. The cells were then exposed to 150 μM MPP$^+$ for 36 hours. For assessment of the cell viability, 15 μl of 5 mg/ml MTT solution was added to each well containing cell in 100 μl of medium, and the plates were incubated for 4 hours in a humidified incubator at 37° C. After incubation, 100 μl of absolute DMSO was added and incubated for 10 min. Absorbance at 570 nm of each well was measured with a microplate reader.

FIG. 1 shows that compounds 1-5 prevented MPP$^+$-induced CGNs damage. Compound 1 shows neuroprotective effect on MPP$^+$-induced primary SD rat CGNs damage in a dose-dependent manner with $E_{max}$ at the concentration of 50 μM. Compound 2 has neuroprotective effect on MPP$^+$-induced primary SD rat CGNs damage with $E_{max}$ at the concentration of 50 μM. Compound 3 has neuroprotective effect on MPP$^+$-induced primary SD rat CGNs damage with $E_{max}$ at the concentration of 25 μM. Compound 4 has neuroprotective effect on MPP$^+$-induced primary SD rat CGNs damage with $E_{max}$ at the concentration of 12 μM. Compound 5 has neuroprotective effect on MPP$^+$-induced primary SD rat CGNs damage in a dose-dependent manner with $E_{max}$ at the concentration of 50 μM.

As presented in FIG. 1, cell viability of CGNs has been significantly increased upon pretreating with different concentrations of compounds 1-5. Thus, FIG. 1 shows that compounds 1-5 can protect against neural damage induced by MPP$^+$, and be used to treat neurodegenerative diseases.

Figures 2A, 2B:
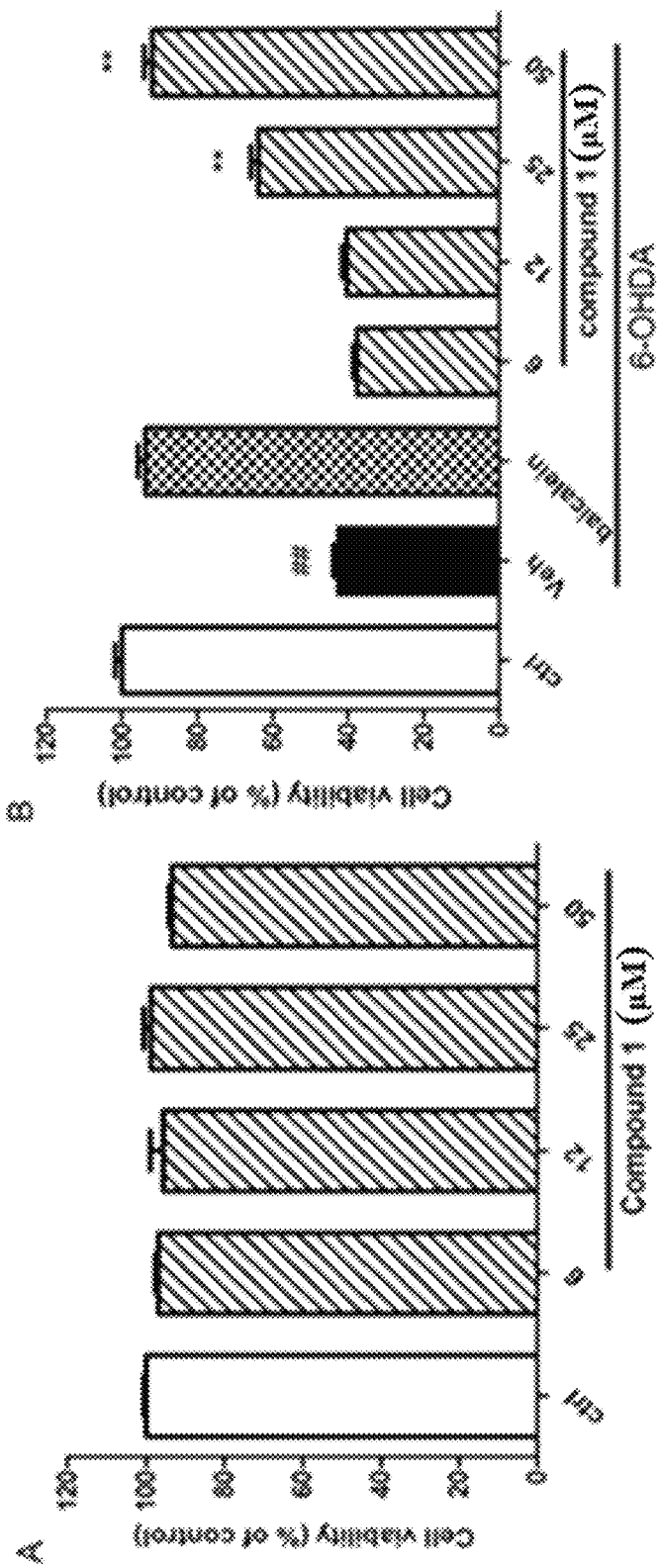
FIG. 2A shows the effect of compound 1 on PC12 cells.
FIG. 2B shows the effects of compound 1 on 6-OHDA-induced PC12 cells damage. $\#\#p<0.01$ versus control group; $**p<0.01$ versus vehicle group.

EXAMPLE 6 Study on the Effects in Protecting PC12 Cells Against 6-OHDA-Induced Neuronal Damage Rat pheochromocytoma cells (PC12) cells were seeded in 100 cm dishes at a density of 1.5~2×10$^6$ cells/dish. After culturing in a medium with a low serum level (F-12K medium with 0.5% FBS) for 24 hours, the cells were pretreated with serial concentrations of compound 1 from 6 μM to 50 μM for 12 hours. The cells were then exposed to 1 mM 6-OHDA for 2 hours. Cell viability of cells was assessed similarly as described in Example 5. As shown in FIG. 2A, PC12 cells pretreated with compound 1 did not exhibit any cytotoxicity at all tested concentrations. 6-OHDA was cytotoxic to PC12 cells but compound 1 could alleviate the cytotoxic effect in a dose-dependent manner as shown in FIG. 2B. Compound 1 exhibited a significant and maximum neuroprotective effect to 6-OHDA treated PC12 at 50 μM. Baicalein, one of the main flavonoids extracted from the root of *Scutellaria baicalensis* Georgi (SBG), has been demonstrated to prevent against neuronal damage induced by 6-OHDA or MPTP in both in vitro and in vivo models of Parkinson's disease (Im, Joo et al. 2005; Lee, Noh et al. 2005; Cheng, He et al. 2008; Mu, He et al. 2009; Mu, He et al. 2011). Here baicalein was used as a positive control, which at the concentration of 100 µM obviously protected PC12 cells against 6-OHDA-induced neuronal damage.

Thus, FIGS. 2A and 2B show that compound 1 can have neroprotective effect to 6-OHDA treated PC12. Further, compound 1 has neuroprotective effect on 6-OHDA-induced PC12 cell damage in a dose-dependent manner with maximum efficacy (Emax) at the concentration of 50 µM.

EXAMPLE 7 Study on the Effect in Attenuating MPTP-induced DA Neuron Injury

Figure 3A:
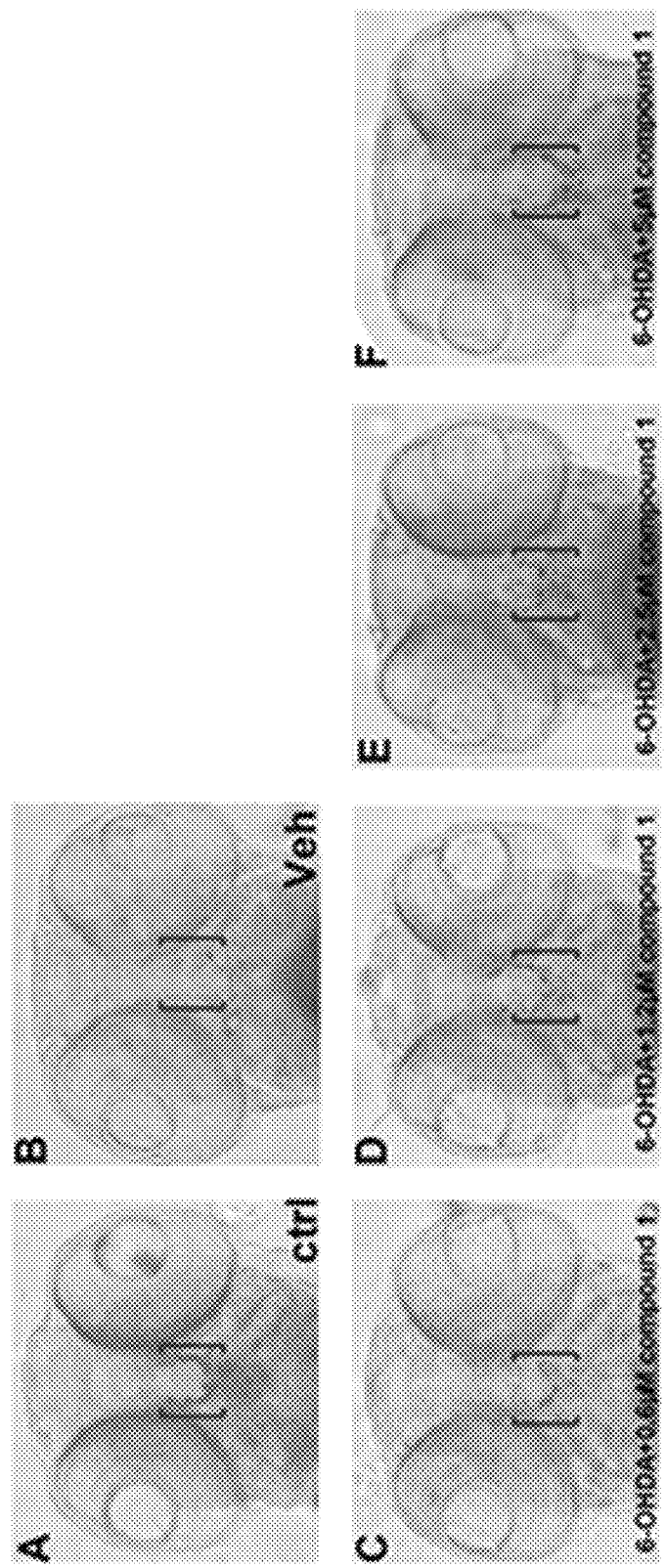
FIG. 3A shows the effects of compound 1 on protecting zebrafish from MPTP-induced dopaminergic neuron loss.
Figure 3B:
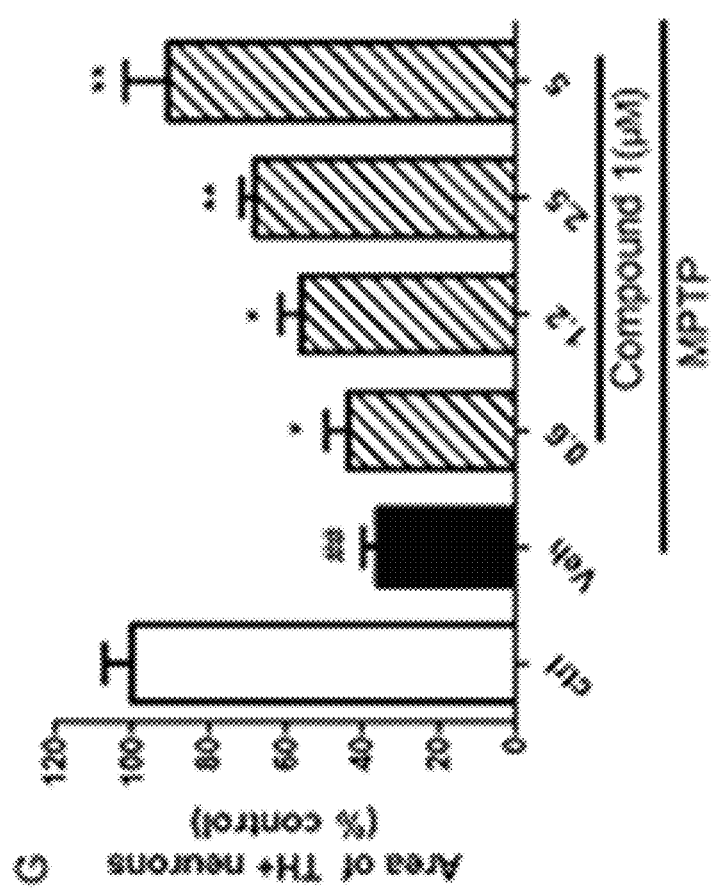
FIG. 3B shows the effects of compound 1 on protecting zebrafish from MPTP-induced dopaminergic neuron loss. $\#\#p<0.01$ versus control group; $*p<0.05$ versus vehicle group; $**p<0.01$ versus vehicle group.

Zebrafish embryo was dechorinated at 1 day post fertilization (dpf) and was cultured under co-treatment of 200 µM MPTP and various concentrations of compound 1 for 48 hours. Afterwards, zebrafish was fixed in 4% paraformaldehyde in PBS for 5 hours, rinsed and stored at −20° C. in 100% EtOH. Whole-mount immunostaining was done by standard methods (Bitzur, Kam et al. 1994). Compound 1 attenuated MPTP-induced DA neuron injury in a dose-dependent manner as shown in FIG. 3A. Further, compound 1 can protect MPTP-induced dopaminergic neuron loss in zebrafish in a dose-dependent manner with $E_{max}$ at the concentration of 5 µM as shown in FIG. 3B in which the results were expressed quantitatively as percentages of area of TH-positive cells in comparison to untreated control group. Thus FIG. 3B shows that compound 1 can protect against TH-positive cells loss.

Figure 4A:
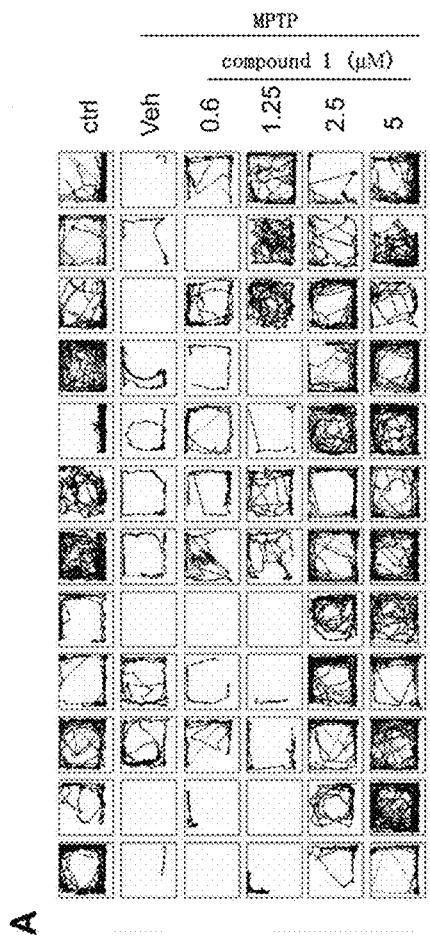
FIG. 4A shows compound 1 reversed decrease of total distance traveled induced by MPTP in the zebrafish.
Figure 4B:
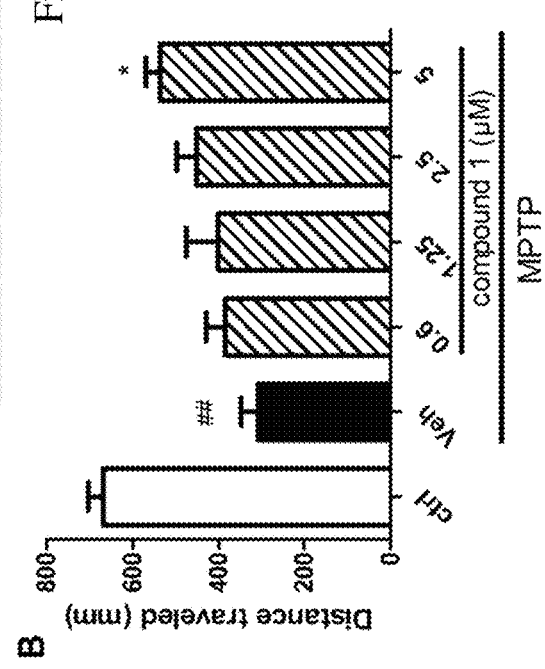
FIG. 4B shows compound 1 reversed decrease of total distance traveled induced by MPTP in the zebrafish. $\#\#p<0.01$ versus control group (without MPTP treatment); $*p<0.05$ versus MPTP-treated group.

EXAMPLE 8 Study on the Effect in Attenuating MPTP-induced Reduction of Total Travelling Distance for Zebrafish Larvae The 3 dpf zebrafish larvae were co-treated with 200 µM MPTP and various concentrations of compound 1 for 4 days. At 7 dpf, the total distance the larvae traveled was recorded using a 96-well plate (with 1 fish/well and 12 larvae per group) filled with 200 µl embryo medium. Larvae were allowed to accommodate in the system for an hour before data acquisition. The swimming pattern of each larva was recorded for 10 min in 3 times, with each record session separated by 10 min. The total distance traveled was estimated as the distance (in mm) that the larva had moved during one session (10 min). As shown in FIGS. 4A and 4B, compound 1 attenuated MPTP-induced reduction of total distance traveled of the larvae in a dose dependent manner.

EXAMPLE 9 Study on Synergistic Neuroprotective Effect of Compound 1 and Chrysin

Primary cerebellar granule neurons (CGNs) were prepared from 8 days old Sprague-Dawley rats as described (Zhang et al., 2012). CGNs that have been cultured in vitro for 7 days were pre-treated with serial concentrations of compound 1 from 3 µg/ml to 50 µg/ml for 2 hours or with 0.1% DMSO (vehicle group). The cell viability was estimated similarly as in Example 5.

Figure 5:
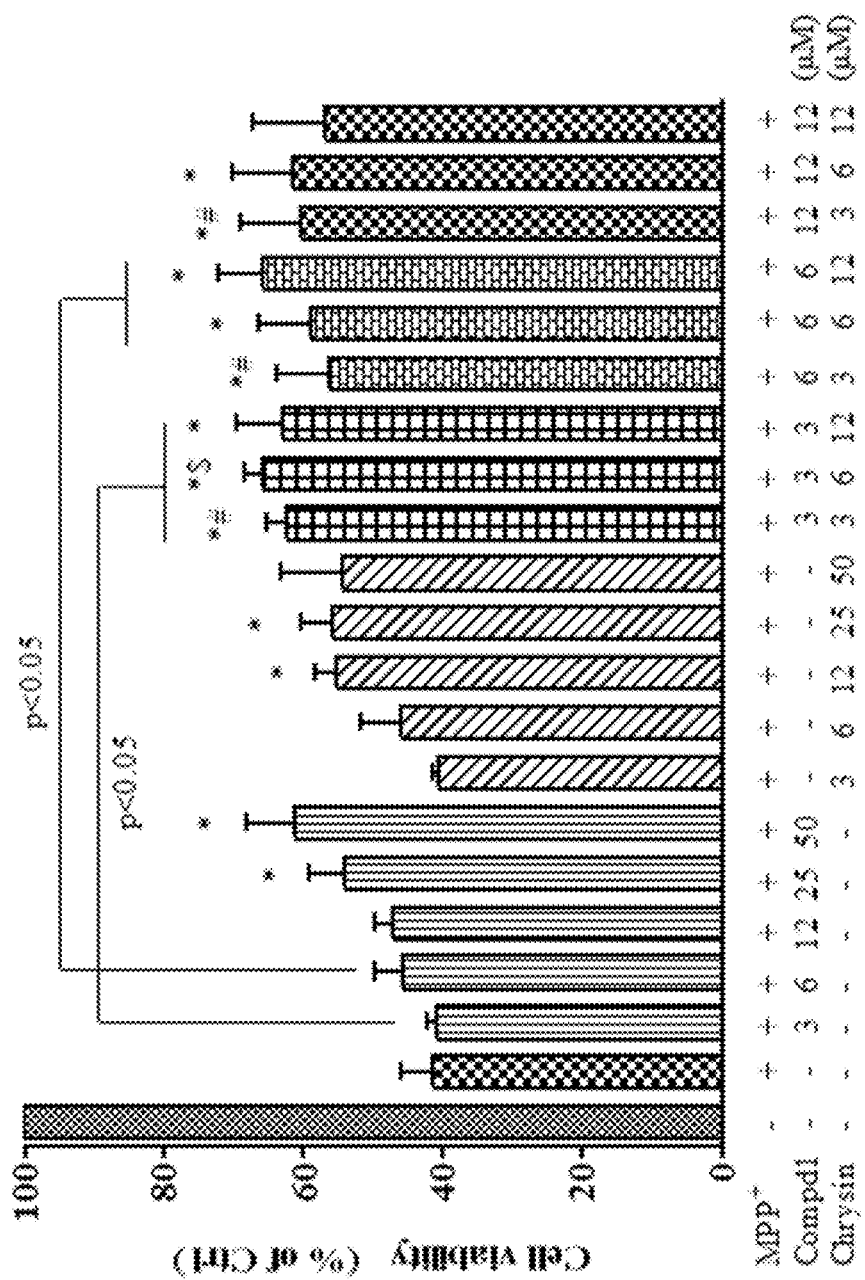
FIG. 5 shows the synergistic neuroprotective effects of compound 1 and chrysin on $MPP^+$-induced primary CGNs damage. $*p<0.05$ compared with $MPP^+$ treatment alone group; $\#p<0.05$ compared with 3 µM chrysin plus $MPP^+$ treatment group; $\$ p<0.05$ compared with 6 µM chrysin plus $MPP^+$ treatment group.

As shown in FIG. 5, both compound 1 and chrysin protected MPP$^+$-induced cell damage in CGNs in a dose-dependent manner. The cell viability was significantly enhanced when the cells were treated with 25 and 50 µM of compound 1 as well as with 12 and 25 µM of chrysin as compared with the control group treated with MPP$^+$ alone ($p<0.05$). CGNs were also co-treated with compound 1 and chrysin to explore the pharmacological interaction between two compounds. It is found that at higher concentrations such as 25 and 50 µM, the co-treatment did not exert any neuroprotective effect but imposed toxicity on the CGNs (data not shown). Conversely, at lower concentrations of 3 and 6 µM, compound 1 and chrysin showed significant synergistic neuroprotective effect as compared with cells treated with MPP$^+$ alone, MPP$^+$/compound 1 and MPP$^+$/chrysin.

EXAMPLE 10 Study of Neuroprotective Effect of Compound 1 in MPTP-Injected Mice

Animals and Drug Treatment

Figure 6:
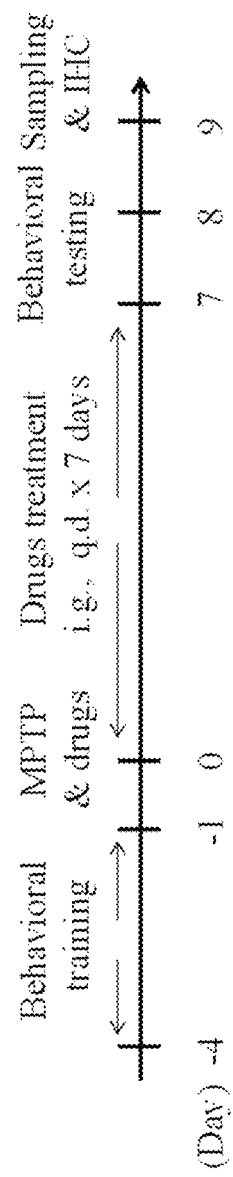
FIG. 6 shows workflow of drug treatments and behavioral testing.

Adult male C57BL/6J mice (8-10 weeks of age, 18-22 g) were used in this study. The animals were maintained in 12/12 h light/dark cycle and allowed access to food and water ad libitum. They were allowed to acclimate for 7 days before treatment. As shown in FIG. 6, all the animals were conducted behavioral training (pole climbing, rotarod running and foot printing) for total 4 days before MPTP injection. Then the mice were injected intraperitoneally (i.p.) with 20 mg/kg MPTP hydrochloride (Sigma Aldrich, St. Louis, Mo.), at 2 h internal for total 4 injections. Normal control group were received saline (0.1 mL/10 g) by i.p. One hour prior each MPTP injection, compound 1 (5, 10 and 20 mg/kg), rasagiline (1 mg/kg) and equal volume of vehicle (olive oil, 0.1 mL/10 g) were administrated by i.g. Then, compound 1, rasagiline or vehicle was given by i.g. once per day for total 7 days (day 1-7). Each of six groups was comprised of 10 mice.

Behavioral Testing

Twenty-four hours after administration of the last dose of drugs (on the day 8 as shown in FIG. 6), mice were observed for neurobehavioral changes by pole test, rotarod test and footprint test. All the tests were done between 9 am and 2 pm under normal animal room lighting.

The pole test was performed to detect impairment of limb movement. A table tennis ball (5 cm diameter) was equipped on the top of a vertical pole (55 cm length and 1 cm diameter). The pole was wrapped with a double layer of gauze to avoid slipping. The animal was placed head upward on the table tennis ball. The time the animal took to climb down to the floor was used to indicate performance. Three-time repeated testes were carried out for each animal and the mean values were used for statistical analysis.

The rotarod test could reveal motor coordination ability. A Rotarod system (YLS-4C, Academy of Medical Sciences of Shandong Province, China) was set at an accelerating program with a starting speed of 5 rpm to a final speed of 40 rpm. Mice were allowed to adjust their posture in order to maintain their balance on a rotating rod during speed accelerating. Infrared beams are used to detect when a mouse has fallen onto the base grid beneath the rotarod. The system logs the fall as the end of the experiment for that mouse, and the total time on the rotarod was recorded. For testing, 5 mice were tested at the same time. The average retention time on the rod was calculated.

In the footprint test, mice with their forepaws and hind paws colored with red ink were trained to walk through a 5 cm-wide, 100-cm-long corridor. Their footsteps were recorded on a white absorbing paper.

Tissue Preparation

Mice were sacrificed for tissue preparation on the day 9 as described in FIG. 6. Mice in each group were anesthetized and perfused intracardially with 0.9% sodium chloride containing heparin, and then fixed with 4% paraformaldehyde (PFA). Each brain was removed, dehydrated with graded alcohol and embedded in paraffin wax, coronally sectioned for 5 μM. The rostral and caudal part of the brain was divided for immunohistochemistry of substantia nigra pars compacta (SNpc).

Anti-Tyrosine Hydroxylase (TH) Immunohistochemistry

The immunohistochemistry was conducted as previously described (Lee, Kim et al. 2011; Levites, Weinreb et al, 2001). Briefly, sections were deparaffinized in xylene and rehydrated in a graded ethanol series. Sections were incubated with 3% hydrogen peroxide ($H_2O_2$) for 10 min at room temperature to inactive endogenous peroxidase activity followed by antigen retrieval in citrate buffer for 15 min in a microwave oven at 95° C. Non-specific protein binding was blocked with 10% bovine serum in PBS (0.01 M, pH 7.4). Between each treatment, the slides were washed at least three times with deionized water for 5 min. Sections were then incubated for 1 h at room temperature with a rabbit anti-mouse TH polyclonal antibody (1:1000; Millipore, USA) diluted in Immunol Staining Primary Antibody Dilution Buffer. Then the sections were incubated with a biotinylated HRP-conjugated secondary antibody for 30 min at room temperature. TH-positive neurons were then visualized using a DAB Kit according to the manufacturer's instructions (Shanghai, Gene Company, China). The peroxidase reaction was stopped after 3 min. Finally, sections were cover slipped with neutral balsam. The results were analyzed by counting the numbers of TH-positive cells at ×10 magnifications on a stereomicroscope (BX51, Olympus Corp. Japan). TH-positive cells in 8 position-matched sections of each mouse were counted manually by operator who was blinded to the drug treatment. The average number of TH-positive cells per section was used to represent dopaminergic neuron livability.

Results

Compound 1 Ameliorated the Movement Impairments of MPTP-treated Mice

Figures 7A, 7B:
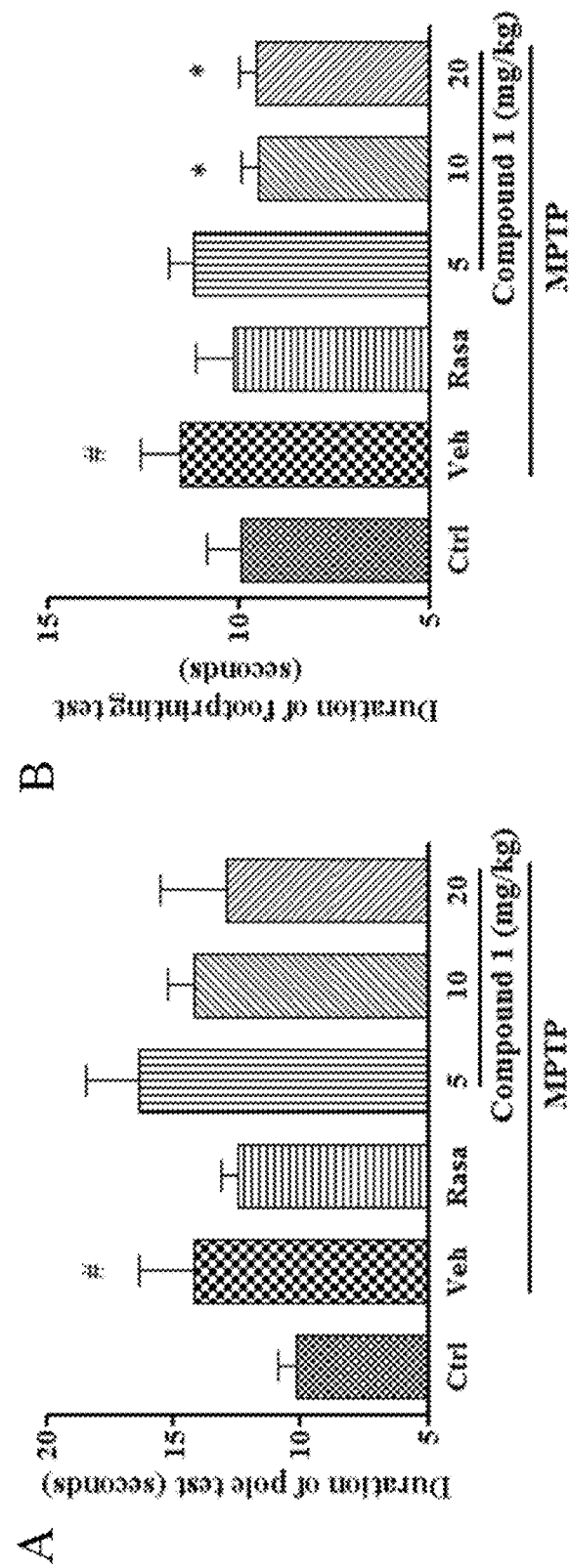
FIG. 7A shows the pole test illustrating compound 1 ameliorated the movement impairment of MPTP-injected mice. Results were presented as mean±S.E.M (n=8) of three repeated tests. #p<0.05 and ###p<0.001 compared with control (Ctrl) group; *p<0.05, p<0.01 and *p<0.001 compared with vehicle (Veh) treatment group. Rasa, rasagiline.
FIG. 7B shows the duration of foot printing test illustrating compound 1 ameliorated the movement impairment of MPTP-injected mice. Results were presented as mean±S.E.M (n=8) of three repeated tests. #p<0.05 and ###p<0.001 compared with control (Ctrl) group; *p<0.05, p<0.01 and *p<0.001 compared with vehicle (Veh) treatment group. Rasa, rasagiline.
Figures 7C, 7D:
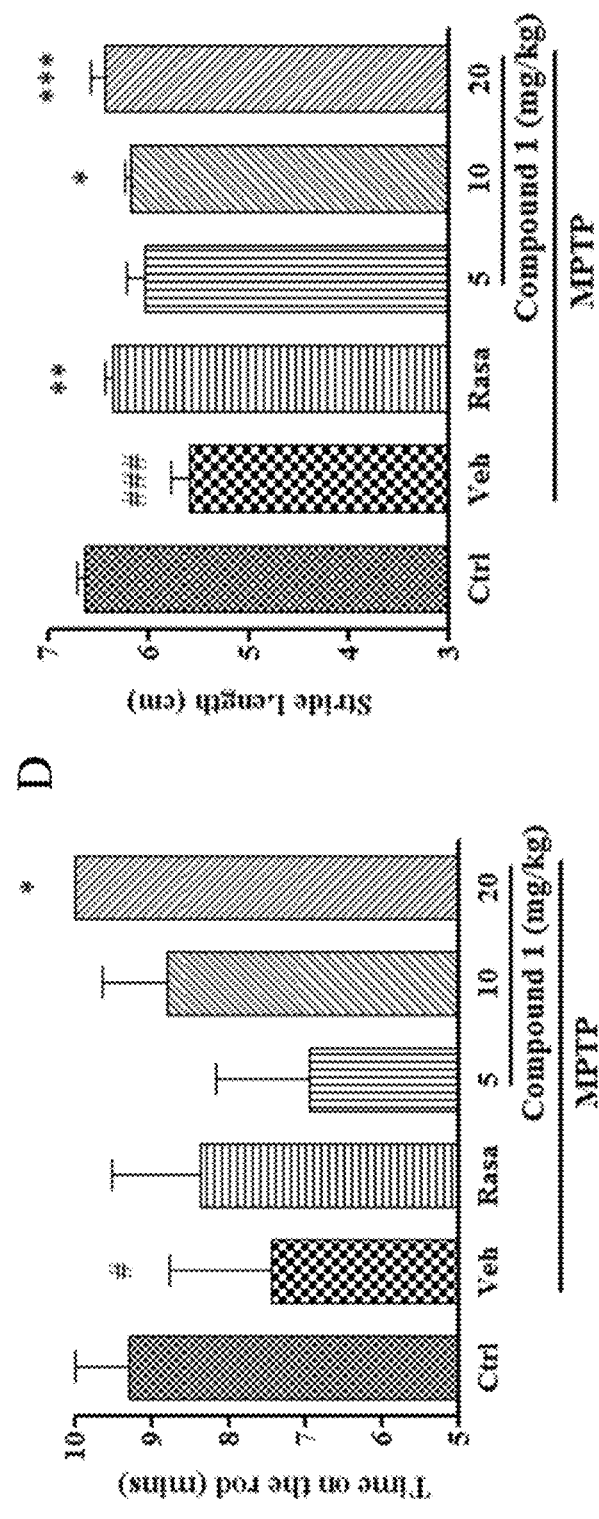
FIG. 7C shows the rotarod test illustrating compound 1 ameliorated the movement impairment of MPTP-injected mice. Results were presented as mean±S.E.M (n=8) of three repeated tests. #p<0.05 and ###p<0.001 compared with control (Ctrl) group; *p<0.05, p<0.01 and *p<0.001 compared with vehicle (Veh) treatment group. Rasa, rasagiline.
FIG. 7D shows the stride length of foot printing test illustrating compound 1 ameliorated the movement impairment of MPTP-injected mice. Results were presented as mean±S.E.M (n=8) of three repeated tests. #p<0.05 and ###p<0.001 compared with control (Ctrl) group; *p<0.05, p<0.01 and *p<0.001 compared with vehicle (Veh) treatment group. Rasa, rasagiline.
Figure 8A:
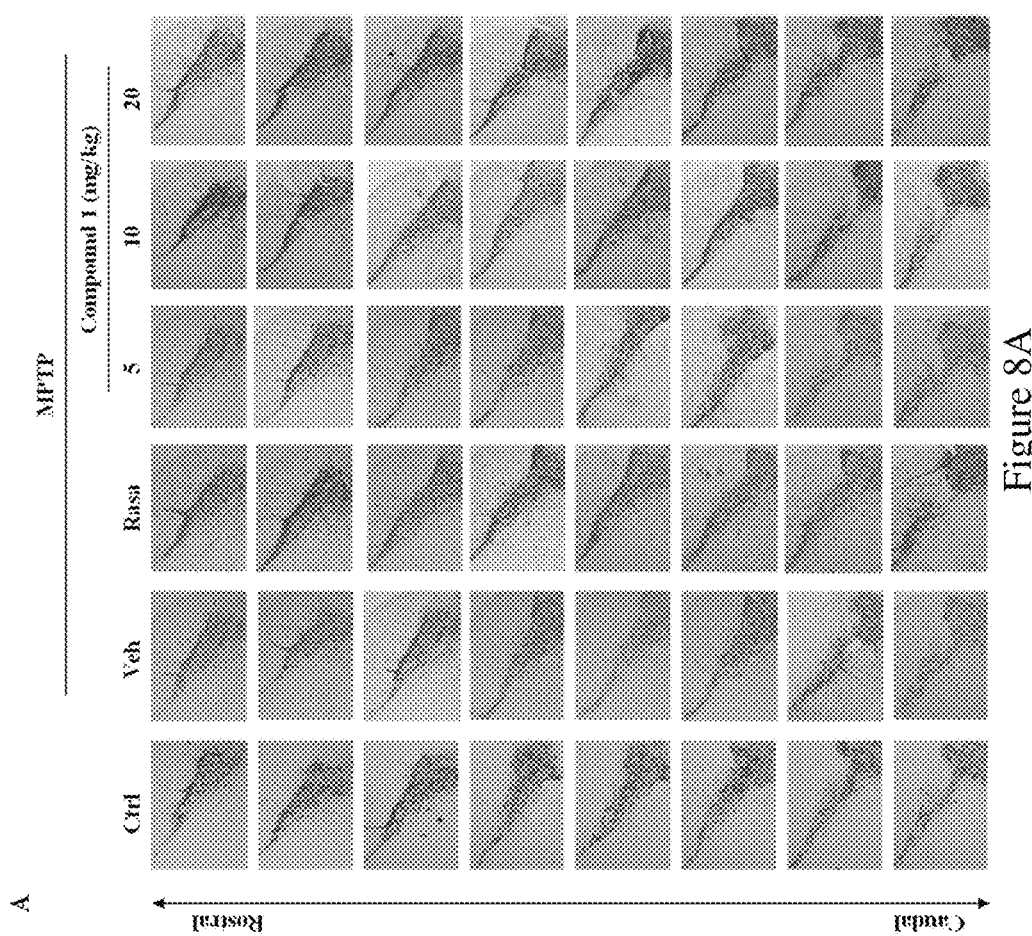
FIG. 8A shows the TH immunostaining of representative midbrain sections from rostral to caudal illustrating compound 1 protected TH-positive dopaminergic neuron loss in the MPTP-injected mice.
Figures 8B, 8C:
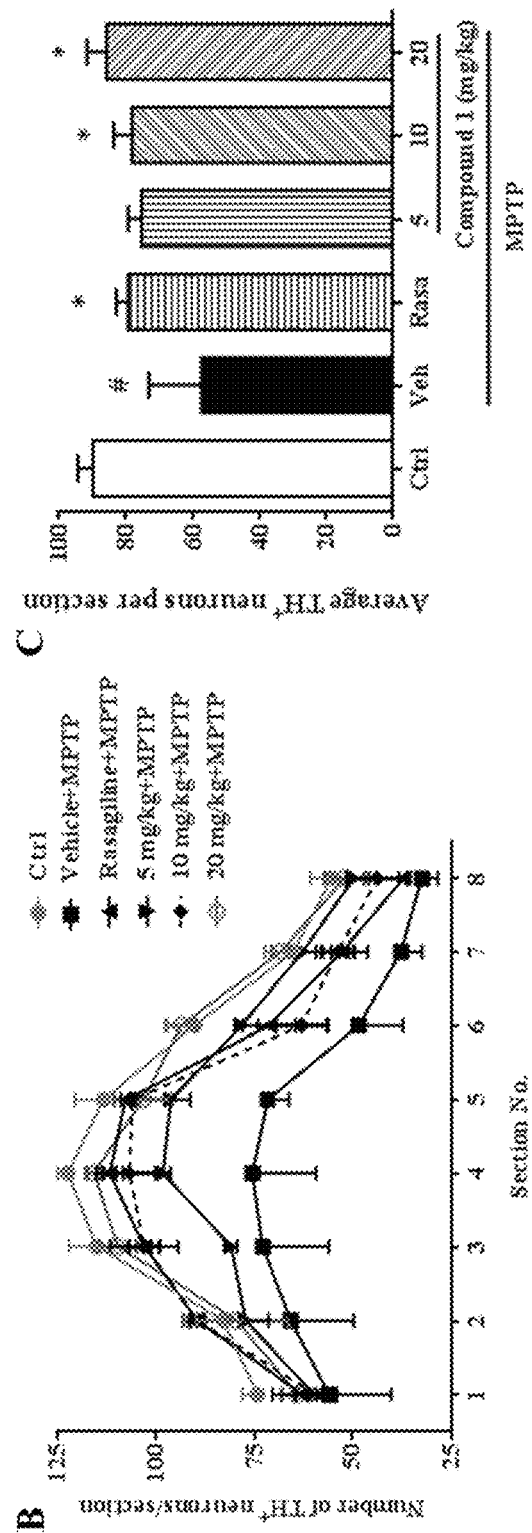
FIG. 8B shows the graph illustrating TH-positive cell counts ±S.E.M (n=8) for the 8 matched adjacent sections.
FIG. 8C shows statistic analysis of average of the data of sections for different treatment groups illustrating compound 1 protected TH-positive dopaminergic neuron loss in the MPTP-injected mice. Results were presented as mean±S.E.M (n=8). #p<0.05 compared with control (Ctrl) group; *p<0.05 compared with vehicle (Veh) treatment group. Rasa, rasagiline.

Loss of SNpc DA neurons contributes to the movement abnormalities observed in PD. The movement of mice following MPTP injection was assessed. FIGS. 7A to 7D showed that MPTP significantly increased the time climbing down from the pole (FIG. 7A), delayed the time of crossing the corridor (FIG. 7B), reduced the time of mice on rotating rotor rod (FIG. 7C) and caused mice to lose their normal gait, shortening stride length (FIG. 7D). As such, FIGS. 7A to 7D show that compound 1 treatment largely corrected the movement abnormalities in a dose-dependent manner Effect of Compound 1 on SNpc DA Neurons Loss of MPTP-treated Mice Injection of MPTP (20 mg/kg) every 2 h for a total of four doses over an 8 h period in 1 d caused about 40% TH-positive DA neurons loss in the SNpc at 7 days post injection, and the loss of TH-positive cells appeared somewhat more marked in the middle than in the rostral and the caudal part (FIGS. 8A and B). Pre- and post-treatment with compound 1 significantly reduced the MPTP-induced TH-positive cell body loss in a dose-dependent manner (FIGS. 8A to 8C). The same schedule was used for rasagiline, a selective MAO-B inhibitor approved for treatment of PD patients, also prevented against the MPTP-induced TH-positive cell body loss.

Conclusion

The present invention provides three isolated and purified compounds: 1 ((R)-4-(2-hydroxy-5-methylphenyl)-5-methylhexanoic acid), 2 ((4S)-4-(3-hydroxy-3-methyl-6-oxocyclohex-1-enyl)-5-methylhexanoic acid) and 3 ((4R)-4-(3-hydroxy-3-methyl-6-oxocyclohex-1-enyl)-5-methylhexanoic acid), isolated from *A. oxyphyllae* fructus, with neuroprotective effect as shown in the above examples; and two synthesized compounds: 4 ((S)-4-(2-hydroxy-5-methylphenyl)-5-methylhexanoic acid) and 5 (4-(2-hydroxy-5-methylphenyl)-5-methylhexanoic acid) with neuroprotective effect. These five lead compounds have neuroprotective effects which could be developed into therapeutic agent for neurodegenerative diseases (e.g. Parkinson's disease). Further, the present invention provides a simple and easy method for extraction and purification of these three novel compounds 1-3 from *A. oxyphyllae* fructus and an elaborated procedure for synthesizing compounds 1, 4 and 5. In vitro neuroprotective activity on CGNs of compounds 1-5 is also presented. Furthermore, this invention shows that compound 1 possesses in vivo and in vitro neuroprotective activities on PC12 cells and zebrafish.

Data presented herein show that, on $MPP^+$ induced primary cultured cerebral granular neurons (CGNs) damage, compounds 1-5 showed concentration dependent neuroprotective effect at concentration of 6-50 μM. Moreover, compound 1 could prevent PC12 cells against 6-OHDA-induced neurotoxicity; protect zebrafish from MPTP-induced dopaminergic neuron loss; and improve the impairment of swimming behavior induced by MPTP in zebrafish. Compound 1 could also ameliorate the movement impairments of MPTP-treated mice and reduce the MPTP-induced TH-positive cell body loss. In addition, compound 1 and chrysin (another known flavonoid compound isolated from *A. oxyphyllae* fructus) showed synergistic neuroprotective effects on $MPP^+$-induced CGNs damage. These results suggest that compounds 1-5 alone or their combination with other neuroactive compounds can be used as a drug for treating neurodegenerative diseases such as Parkinson's disease.

In addition to the single compound method of treatment described above, the combination of compound 1 and chrysin show synergistic effect. One skilled in the art in the course of developing a treatment regime will be able to determine the optimal therapeutic dose to administer to a patient either using one of the above compounds or in combination without undue experimentation.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

All references cited above and in the following description are incorporated by reference herein. The practice of the invention is exemplified in the following non-limiting examples. The scope of the invention is defined solely by the appended claims, which are in no way limited by the content or scope of the examples.

REFERENCES

An, L., S. Guan, et al. (2006). "Protocatechuic acid from *Alpinia oxyphylla* against MPP+-induced neurotoxicity in PC12 cells." Food and chemical toxicology 44(3): 436-443.

Bitzur, S., Z. Kam, et al. (1994). "Structure and distribution of N-cadherin in developing zebrafish embryos: morphogenetic effects of ectopic over-expression." Dev Dyn 201(2): 121-136.

Cheng, Y., G. He, et al. (2008). "Neuroprotective effect of baicalein against MPTP neurotoxicity: behavioral, biochemical and immunohistochemical profile." Neurosci Lett 441(1): 16-20.

Du, Y., K. R. Bales, et al. (1997). "Activation of a caspase 3-related cysteine protease is required for glutamate-mediated apoptosis of cultured cerebellar granule neurons." Proceedings of the National Academy of Sciences 94(21): 11657-11662.

Graziose, R., M. A. Lila, et al. (2010). "Merging traditional Chinese medicine with modern drug discovery technologies to find novel drugs and functional foods." Curr Drug Discov Technol 7(1): 2-12.

Im, H. I., W. S. Joo, et al. (2005). "Baicalein prevents 6-hydroxydopamine-induced dopaminergic dysfunction and lipid peroxidation in mice." J Pharmacol Sci 98(2): 185-189.

Lee, D. H., C. S. Kim, et al. (2011) Astaxanthin protects against MPTP/MPP+-induced mitochondrial dysfunction and ROS production in vivo and in vitro. Food Chem Toxicol 49(1):271-280.

Lee, H. J., Y. H. Noh, et al. (2005). "Baicalein attenuates 6-hydroxydopamine-induced neurotoxicity in SH-SY5Y cells." Eur J Cell Biol 84(11): 897-905.

Levites Y., O. Weinreb, et al. (2001) Green tea polyphenol (−)-epigallocatechin-3-gallate prevents N-methyl-4-phenyl-1,2,3,6-tetrahydropyridine-induced dopaminergic neurodegeneration. J Neurochem 78(5):1073-1082.

Li, W., M. Mak, et al. (2009). "Novel anti-Alzheimer's dimer Bis(7)-cognitin: cellular and molecular mechanisms of neuroprotection through multiple targets." Neurotherapeutics 6(1): 187-201.

Lin, M. T. and M. F. Beal (2006). "Mitochondrial dysfunction and oxidative stress in neurodegenerative diseases." Nature 443(7113): 787-795.

Mandel, S., T. Amit, et al. (2007). "Iron dysregulation in Alzheimer's disease: multimodal brain permeable iron chelating drugs, possessing neuroprotective-neurorescue and amyloid precursor protein-processing regulatory activities as therapeutic agents." Prog Neurobiol 82(6): 348-360.

Mu, X., G. He, et al. (2009). "Baicalein exerts neuroprotective effects in 6-hydroxydopamine-induced experimental parkinsonism in vivo and in vitro." Pharmacol Biochem Behav 92(4): 642-648.

Mu, X., G. R. He, et al. (2011). "Baicalein protects the brain against neuron impairments induced by MPTP in C57BL/6 mice." Pharmacol Biochem Behav 98(2): 286-291.

Yang, M., J. Sun, et al. (2009). "Phytochemical analysis of traditional Chinese medicine using liquid chromatography coupled with mass spectrometry." Journal of Chromatography A 1216(11): 2045-2062.

Zhang, X., G. F. Shi, et al. (2011). "Anti-ageing effects of protocatechuic acid from *Alpinia* on spleen and liver antioxidative system of senescent mice." Cell Biochemistry and Function 29(4): 342-347.

Zhang, Z. J., L. C. V. Cheang, et al. (2012). "Ethanolic Extract of Fructus *Alpinia oxyphylla* Protects Against 6-Hydroxydopamine-Induced Damage of PC12 Cells In Vitro and Dopaminergic Neurons in Zebrafish." Cellular and molecular neurobiology 32(1): 27-40.

What is claimed is:

1. A method of treating Parkinson's disease in a patient, the method comprising:
   administering a compound to the patient to treat the Parkinson's disease,
   wherein the compound is selected from a group consisting of ((R)-4-(2-hydroxy-5-methylphenyl)-5-methylhexanoic acid), ((S)-4-(2-hydroxy-5-methylphenyl)-5-methylhexanoic acid) and (4-(2-hydroxy-5-methylphenyl)-5-methylhexanoic acid).

2. The method of claim 1, wherein the compound and chrysin are provided to the patient, and the compound and the chrysin exhibit a synergistic effect for treating the Parkinson's disease.

3. A method of protecting against neural damage in a subject in need thereof, the method comprising:
   administering a compound to the subject to protect against the neural damage,
   wherein the compound is selected from a group consisting of ((R)-4-(2-hydroxy-5-methylphenyl)-5-methylhexanoic acid), ((S)-4-(2-hydroxy-5-methylphenyl)-5-methylhexanoic acid) and (4-(2-hydroxy-5-methylphenyl)-5-methylhexanoic acid).

4. The method of claim 3, wherein the compound and chrysin are provided to the subject, and the compound and the chrysin exhibit a synergistic effect for protecting against the neural damage.

5. The method of claim 3, wherein the compound protects against the neural damage in cerebellar granule neurons.

6. The method of claim 3, wherein the compound protects against the neural damage in pheochromocytoma cells.

7. A method of protecting against neural cell loss in a subject in need thereof, the method comprising:
   administering a compound to the subject to protect against the neural cell loss,
   wherein the compound is selected from a group consisting of ((R)-4-(2-hydroxy-5-methylphenyl)-5-methylhexanoic acid), ((S)-4-(2-hydroxy-5-methylphenyl)-5-methylhexanoic acid) and (4-(2-hydroxy-5-methylphenyl)-5-methylhexanoic acid).

8. The method of claim 7, wherein the compound and chrysin are provided to the subject, and the compound and the chrysin exhibit a synergistic effect for protecting against the neural cell loss.

9. The method of claim 7, wherein the compound protects against the neural cell loss in dopaminergic neurons.

* * * * *